(12) United States Patent
Philippe et al.

(10) Patent No.: US 7,316,815 B2
(45) Date of Patent: Jan. 8, 2008

(54) POLYAMINO ACID DERIVATIVES AND USE THEREOF IN COMPOSITIONS FOR TREATING KERATIN FIBERS

(75) Inventors: Michel Philippe, Wissous (FR); Christian Blaise, Saint Mandé (FR)

(73) Assignee: L'Oreal S.A., Paris (FR)

(\*) Notice: Subject to any disclaimer, the term of this patent is extended or adjusted under 35 U.S.C. 154(b) by 508 days.

(21) Appl. No.: 10/682,783

(22) Filed: Oct. 10, 2003

(65) Prior Publication Data

US 2004/0091442 A1    May 13, 2004

Related U.S. Application Data

(63) Continuation of application No. 09/647,493, filed as application No. PCT/FR99/00256 on Feb. 5, 1999, now Pat. No. 6,656,458.

(30) Foreign Application Priority Data

Mar. 31, 1998    (FR) .................................. 98 03965

(51) Int. Cl.
*A61K 8/02*    (2006.01)
*A61K 8/73*    (2006.01)
*A61K 31/74*   (2006.01)
*A61K 31/28*   (2006.01)
*A61K 31/16*   (2006.01)

(52) U.S. Cl. ................ 424/401; 424/70.17; 424/78.02; 514/506; 514/626; 514/881; 514/937; 514/944; 514/945

(58) Field of Classification Search ................ 514/506, 514/626, 881, 937, 944, 945; 424/401, 70.17, 424/78.02
See application file for complete search history.

(56) References Cited

U.S. PATENT DOCUMENTS

| | | | |
|---|---|---|---|
| 4,186,188 A | 1/1980 | Gumprecht | |
| 4,396,152 A | 8/1983 | Abplanalp | |
| 4,600,526 A | 7/1986 | Gallot et al. | |
| 4,761,273 A | 8/1988 | Grollier et al. | |
| 5,286,475 A | 2/1994 | Louvet et al. | |
| 5,384,114 A | 1/1995 | Dowell et al. | 424/70.1 |
| 5,595,727 A | 1/1997 | Sturla | |
| 5,653,963 A * | 8/1997 | Beitone et al. | 424/47 |
| 5,665,778 A | 9/1997 | Semeria et al. | 514/613 |
| 5,686,066 A | 11/1997 | Harada et al. | 424/70.1 |
| 5,798,121 A | 8/1998 | Cauwet et al. | |
| 5,830,438 A | 11/1998 | Dupuis | |
| 5,925,728 A | 7/1999 | Kim et al. | |
| 6,010,707 A | 1/2000 | Philippe et al. | 424/401 |
| 6,039,963 A | 3/2000 | Philippe et al. | 424/401 |
| 6,086,903 A | 7/2000 | Trinh et al. | 424/401 |
| 6,184,252 B1 | 2/2001 | Fagot et al. | 514/625 |
| 6,335,024 B2 | 1/2002 | Philippe et al. | 424/401 |
| 2001/0036914 A1 | 11/2001 | Philippe et al. | 514/2 |
| 2001/0043935 A1 | 11/2001 | Philippe et al. | 424/401 |
| 2002/0164360 A9 * | 11/2002 | Philippe et al. | 424/401 |

FOREIGN PATENT DOCUMENTS

| | | |
|---|---|---|
| DE | 26 53 560 | 6/1977 |
| EP | 0 774 247 A2 | 5/1997 |
| FR | 2 382 637 | 9/1978 |
| FR | 2 505 348 | 11/1982 |
| FR | 2 533 209 | 3/1984 |
| FR | 2 533 222 | 3/1984 |
| FR | 2 668 927 | 5/1992 |
| FR | 2 684 874 | 6/1993 |
| FR | 2 719 995 | 11/1995 |
| FR | 2 728 163 | 6/1996 |

(Continued)

OTHER PUBLICATIONS

Gallot et al., "Liquid crystalline phases and emulsifying properties of block copolymer hydrophobic aliphatic and hydrophilic peptide chains," ACS Symp. Ser. (1989), 384 (Polym. Assoc. Struct), 116-28.

Derwent Publications Ltd., London, GB; AN 98-551188, XP002092506, JP 10 245396.

Derwent Publications Ltd., London, GB; AN 99-018385, XP002092507, JP 10 287697.

(Continued)

*Primary Examiner*—Sreeni Padmanabhan
*Assistant Examiner*—Renee Claytor
(74) *Attorney, Agent, or Firm*—Finnegan, Henderson, Farabow, Garrett & Dunner

(57) ABSTRACT

The invention concerns the use in a cosmetic composition of at least a poly-aminoacid of general formula (I) in which X is —O—, —S— or —NR$_3$; R$_1$ represents in particular a hydrogen atom or a C$_1$-C$_{40}$ alkyl radical; R$_2$ represents in particular a hydrogen atom or an optionally substituted alkyl radical; R$_3$ represents a hydrogen atom or an alkyl radical; R$_4$ represents a hydrogen atom or a radical such as NH$_2$, OH, SH, —CHOHCH$_3$, —CONH$_2$; n is a number greater than 1 such that the poly-aminoacid derivative molecular weight ranges between 200 and 200000. The invention also concerns the use of said derivatives for keratinous fibre strengthening and care

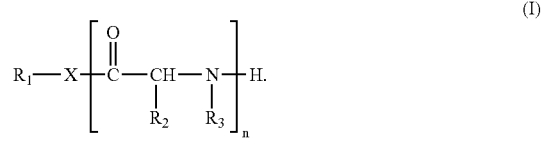

30 Claims, No Drawings

FOREIGN PATENT DOCUMENTS

| | | |
|---|---|---|
| FR | 2 744 912 | 8/1997 |
| JP | 05255058 | 10/1993 |
| JP | 6-248072 | 9/1994 |
| JP | 408245333 | 9/1996 |

OTHER PUBLICATIONS

English language Derwent Abstract of FR 2 533 222.
English language Derwent Abstract of JP 6-248072.
Toshimi Shimizu et al., "Self-assembling Properties of Synthetic Peptidic Lipids", Biochimica et Biophysica Acta., vol. 1147, No. 1, 1993, pp. 50-58.
Derwent Publications Ltd., London, GB; AN 89-117235, XP002092501, JP 01 061412.
Derwent Publications Ltd., London, GB; AN 92-288870, XP002092502, JP 04 198114.
Derwent Publications Ltd., London, GB; AN 97-532840, XP002092503, JP 09 255778.
Derwent Publications Ltd., London, GB; AN 95-118690, XP002092504, JP 07 041467.
Derwent Publications Ltd., London, GB; AN 90-119695, XP002092505, JP 02 069498.

* cited by examiner

POLYAMINO ACID DERIVATIVES AND USE THEREOF IN COMPOSITIONS FOR TREATING KERATIN FIBERS

This is a continuation of application Ser. No. 09/647,493, filed Dec. 14, 2000, now U.S. Pat. No. 6,656,458 which claims the benefit of prior PCT Application No. PCT/FR99/00256, filed Feb. 5, 1999 all of which are incorporated herein by reference.

The present invention relates to the use of polyamino acid derivatives in a cosmetic composition to strengthen and care for keratin fibres, in particular the hair.

The present invention also relates to a "direct" or "in-situ" treatment process to strengthen and care for keratin fibres.

The expression "direct process" means the treatment of the fibres by applying to them a cosmetic composition containing, in a cosmetically acceptable vehicle, at least one pre-synthesized polyamino acid derivative.

The expression "in-situ process" means the treatment of the fibres using precursors which generate a polyamino acid derivative in these fibres.

Different classes of polyamino acids have been described, and their use is well known and widely practised, in particular for their moisturizing properties.

In this respect, Japanese patent application JP-07/041 467 discloses a class of polyamino acids of high molecular weight consisting essentially of cysteine, as well as to the process for preparing these polyamino acids.

A class of polyamino acids characterized by the presence of thiol and/or disulphide functions has also been disclosed in Japanese patent application JP-06/248 072. These polyamino acids react with the thiol linkages of keratin, thus forming disulphide bridges, which makes it possible to increase the sheen and coloration qualities of the hair.

Another class of polyamino acids has been disclosed in Japanese patent application JP-04/198 114, these compounds consisting essentially of amino acids containing neutral and acidic chains, and are generally used as moisturizing agents.

Finally, French patent application FR-2 533 209 discloses amphipathic lipopeptides consisting of a hydrophilic peptide chain and a hydrophobic chain of 8 to 24 carbon atoms, as well as to their use as emulsifiers for immiscible media or for producing liquid crystals.

After numerous studies carried out on various classes of polyamino acids, it has been found, surprisingly and unexpectedly, that one particular class of polyamino acid derivatives has considerable properties in terms of strengthening keratin fibres, resulting from the formation of a substantial deposit of polypeptide material on the surface of the keratin fibres.

The use of these polyamino acid derivatives in cosmetic hair compositions moreover makes it possible to improve the hold and volume of the hair.

One subject of the present invention is thus the use, in a cosmetic composition for strengthening keratin fibres, of at least one polyamino acid derivative of general formula (I) below:

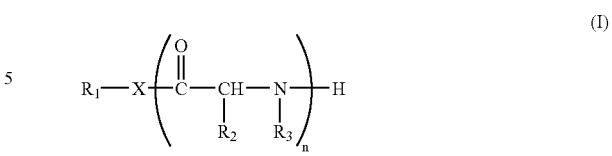

in which:
X is —O—, —S— or —$NR_3$—
$R_1$ represents:
(i) a hydrogen atom, and preferably
(ii) a linear or branched, saturated or unsaturated, $C_1$-$C_{40}$ alkyl radical, optionally substituted with at least one hydroxyl or a radical

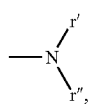

and/or optionally interrupted with at least one hetero atom chosen from N, O or Si, r' and r", which may be identical or different, being a hydrogen atom or a $C_1$-$C_6$ alkyl radical,

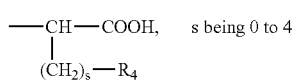

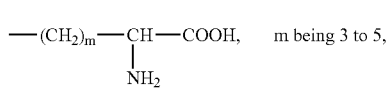

$R_2$ represents a hydrogen atom or a $C_1$-$C_8$ alkyl, —$CH_2C_6H_5$, —$CH_2C_6H_5$p-OH, —$CH_2OH$, —CHOH—$CH_3$ or —$(CH_2)_t$—$NH_2$ radical, t being 3 to 5,
$R_3$ represents a hydrogen atom or a $C_1$-$C_6$ alkyl radical,
$R_4$ represents a hydrogen atom, —$NH_2$, —OH, —SH, —$CHOHCH_3$, —$CONH_2$,

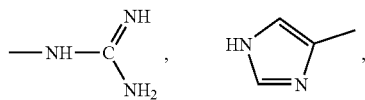

—$C_6H_5$ or —$C_6H_5$p-OH, and
n is an average number greater than 1 such that the molecular weight of the polyamino acid derivative is between 200 and 200,000, the repeating unit being either identical for the same derivative, or different, $R_2$ and/or $R_3$ then taking at least one of the other meanings given for these radicals,
or of a salt of the said polyamino acid derivative.

According to one preferred embodiment, the radical $R_1$ is other than a hydrogen atom.

The polyamino acids of formula (I) are known in certain cases and novel in other cases.

The process for preparing them consists of a polycondensation reaction between at least one N-carboxyanhydride or formula:

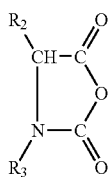
(II)

in which:

R₂ and R₃ have the same meanings as those given above for formula (I), and a nucleophilic compound of formula (III):

(III)

in which R₁ and X have the same meanings as those given above for formula (I).

The N-carboxyanhydrides of formula (II) are prepared by the usual methods, by reacting a D and/or L-α-amino acid with phosgene in an inert solvent such as dioxane or tetrahydrofuran (THF).

The polycondensation reaction is generally carried out at a temperature of between about 0° C. and 120° C. in an inert solvent chosen from benzene, toluene, chlorobenzene, dichloroethane, dimethylacetamide (DMAC), dimethylformamide (DMF), methyl ethyl ketone (MEK), aliphatic ethers such as ethyl ether, isopropyl ether and tert-butyl methyl ether, and cyclic ethers such as tetrahydrofuran and dioxane. However, the reaction solvent can optionally be water.

The formation of a more or less pronounced evolution of $CO_2$ can be observed from the start of the reaction.

After optionally cooling the reaction medium, the solvent is evaporated off and the polyamino acid derivative obtained is then dried under vacuum.

Depending on the purity obtained, a purification step such as a precipitation or a crystallization of the crude product obtained can be carried out.

In the process for preparing the polyamino acid derivative as described above, the nucleophilic compound acts as an initiator for the polycondensation reaction.

According to one preferred embodiment, the molar amount of the nucleophilic compound of formula (III) is 1/2-1/3000, preferably 1/5-1/2000 per mole of the N-carboxyanhydride of formula (II).

Among the N-carboxyanhydrides of formula (II) which may be mentioned in particular are:
glycine N-carboxyanhydride,
sarcosine N-carboxyanhydride,
threonine N-carboxyanhydride,
serine N-carboxyanhydride,
valine N-carboxyanhydride,
norvaline N-carboxyanhydride,
isoleucine N-carboxyanhydride,
leucine N-carboxyanhydride,
norleucine N-carboxyanhydride,
lysine N-carboxyanhydride,
phenylalanine N-carboxyanhydride,
tyrosine N-carboxyanhydride, and
the above N-carboxyanhydrides optionally in protected form.

Among the nucleophilic compounds of formula (III) which may be mentioned in particular are amines such as 2-aminooctadecane-1,3-diol, 2-octyldodecylamine, hexylamine, oleylamine, glucamine, lysine, arginine, histidine and glutamine, alcohols in alkoxide form such as sodium methoxide, and thiols such as cysteine.

The compositions according to the invention can be in various forms and can contain the polyamino acid derivative in a proportion generally of between 0.001% and 30% and preferably between 0.01% and 15% by weight relative to the total weight of the composition.

According to a first embodiment of the compositions according to the invention, they are in the form of a shampoo or a pre- or post-shampoo care composition for strengthening keratin fibres.

The cosmetically acceptable vehicle for these compositions is either an aqueous medium or an aqueous-alcoholic medium containing an alcohol such as ethanol or isopropanol.

The compositions in the form of a shampoo also contain at least one anionic, nonionic, zwitterionic, amphoteric or cationic surfactant.

The proportion of surfactant is generally between 0.01% and 50% by weight, but preferably between 0.05% and 30% by weight, relative to the total weight of the composition.

When a surfactant of the nonionic type is used, it is generally used in a proportion of between 0.1% and 40% by weight, and preferably between 1% and 20% by weight, relative to the total weight of the composition.

On account of the weaker detergent power of the surfactants of cationic type, they are used more particularly in the pre- or post-shampoo care compositions.

The surfactants which can be used in the compositions according to this embodiment are well known in the prior art and have been described in particular in patent FR-2 728 163.

These pre- or post-shampoo care compositions can also contain a conditioner.

As conditioners which can be used in the compositions according to the invention, mention may be made in particular of hydrogenated or non-hydrogenated natural oils, saturated or unsaturated, linear or branched, cyclic or aliphatic, hydrocarbon-based synthetic oils such as, for example, poly-α-olefins, in particular polydecenes and polyisobutenes, soluble or insoluble, organomodified or otherwise, volatile or non-volatile silicone oils, fluoro oils, perfluoro oils, fatty esters, esters of polyhydric alcohols and glycerides.

Synthetic or natural waxes, silicone gums and resins, quaternized or non-quaternized proteins or protein hydrolysates or a mixture of these various agents can also be used as conditioners.

The compositions according to this first embodiment can also contain at least one cosmetically or dermatologically acceptable additive chosen from a thickener, a polymer of cationic, anionic, nonionic or amphoteric type, a sunscreen, a ceramide, an α-hydroxy acid, a preserving agent, an antimicrobial agent, an anti-dandruff agent, a pearlescent agent, a dye, a fragrance, an electrolyte or a suspension agent.

The additives are generally present in the compositions according to the invention in a proportion of between 0.01% and 20% by weight, and preferably between 0.02% and 10% by weight, relative to the total weight of the composition.

The pH of the compositions according to the invention is generally less than 7 and preferably between 3 and 4.5.

According to a second embodiment of the compositions according to the invention, they are in the form of a composition for forming a mousse of anhydrous or aqueous type.

When the mousse composition is of anhydrous type, it comprises a fatty phase as cosmetically acceptable vehicle, a foaming agent and a propellant.

Among the oils and waxes which can be used, mentioned may be made in particular of those of plant, animal, mineral or synthetic origin. These oils and waxes are well known in the prior art and are described in particular in patent FR-2 668 927.

The cosmetic oil or the mixture of oil and wax is generally present in a proportion of between 20% and 99% by weight, but preferably between 25% and 85% by weight, relative to the total weight of the fatty phase.

When the mousse composition is of aqueous type, it comprises an aqueous solution or an aqueous-alcoholic mixture as cosmetically acceptable vehicle, a foaming agent and a propellant.

The aqueous-alcoholic mixture can contain, for example, a $C_1$-$C_4$ alcohol such as ethanol or isopropanol.

When an aqueous-alcoholic solution is used, the proportion of alcohol does not exceed about 50% and is preferably less than 30% by weight relative to the total weight of the composition.

Among the foaming agents or surfactants which can be used, mention may be made, inter alia, of anionic, nonionic, zwitterionic, amphoteric and cationic surfactants. Mention may also be made of cationic or anionic polymers such as those described in patent application FR-82/07996, or alternatively the combination of cationic and amphoteric polymers as described in patent application FR-96/02125.

The proportion of foaming agent can be between 0.05% and 20% by weight, preferably between 0.2% and 10% by weight and more particularly between 0.25% and 5% by weight, relative to the total weight of the composition.

The mousse compositions of aqueous type can also contain a plasticizer in a proportion of between 0.01% and 16% by weight relative to the total weight of the composition.

The plasticizers which can be used are well known and are described in particular in patent FR-2 719 995.

Among the ingredients which can be added to the mousse compositions, mention may be made of dyes, whose function is to colour the composition itself or the hair, preserving agents, sequestering agents, pH regulators, fragrances, vitamins, plant and animal extracts, silicones, sunscreens and other agents for treating keratin fibres.

Among the propellants preferably used in these mousse compositions, mention may be made, for example, of compressed air, carbon dioxide, nitrous oxide, nitrogen, dimethyl ether, liquefiable aliphatic hydrocarbons such as propane, butanes including isobutane, pentane, isopentane, neopentane and mixtures thereof, chlorohydrocarbons and/or fluorohydrocarbons, or mixtures thereof.

Among the chlorohydrocarbons and/or fluorohydrocarbons which may be mentioned are monochlorodifluoromethane, dichlorodifluoromethane, monochlorodifluoroethane, 1,1-difluoroethane and dichlorotetrafluoroethane, as well as mixtures thereof and in particular the mixture of monochlorodifluoro-methane/monochlorodifluoroethane (40/60) as well as the mixture of dichlorodifluoromethane/dichlorotetrafluoro-ethane (60/40).

The proportion of propellant used is not critical, but it determines the density of the foam produced. The higher the proportion of propellant, the lower the foam density. Generally, the foam densities are in the range from about 0.02 g/cm$^3$ to about 0.20 g/cm$^3$ and preferably from about 0.05 g/cm$^3$ to about 0.15 g/cm$^3$.

The proportion of propellant is generally between 1% and 20% by weight relative to the total weight of the aerosol composition, and preferably between 5% and 15%.

The internal pressure in the aerosol container is generally between about 1 and 4 bar ($10^5$ to $4\times10^5$ Pa).

Any type of container and valve system for an aerosol foam is suitable for carrying out the invention according to this embodiment.

According to a third embodiment of the compositions according to the invention, they are in the form of dispersion or an emulsion of the oil-in-water or water-in-oil type, and more particularly in the form of a microemulsion or gel.

The aqueous phase is generally present in a proportion of between 60% and 90% for the oil-in-water emulsions and between 30% and 60% for the water-in-oil emulsions, by weight relative to the total weight of the composition.

The fatty phase is generally present in a proportion of between 5% and 25% for the emulsions of oil-in-water type, and between 30% and 50% for the emulsions of water-in-oil type, by weight relative to the total weight of the composition.

The fatty phase consists of at least one cosmetic oil or a mixture of at least one oil and at least one wax, these being of mineral, plant, animal or synthetic origin, as described in patent FR-2 668 927.

Among the emulsifiers which can be used in the compositions in the form of an oil-in-water emulsion, mention may be made, inter alia, of lauryl sulphate, triethanolamine stearate or fatty alcohols such as stearyl alcohol or cetyl alcohol.

Among the emulsifiers which can be used in the compositions in the form of a water-in-oil emulsion, mention may be made, inter alia, of glycerol esters, ethoxylated alcohols, lanolin, lanolin alcohol, cholesterol and various sorbitan oleates.

The emulsifiers are generally present in a proportion of between 1% and 10% by weight relative to the total weight of the composition.

According to this embodiment, the compositions are preferably transparent microemulsions or gels, and contain an excess of emulsifier and at least one mineral oil of low viscosity.

The mineral oils which can be used in the gel compositions contain short carbon-based chains and are present in a proportion of between 15% and 20% by weight relative to the total weight of the composition.

Among the emulsifiers for the compositions in gel form which may be mentioned in particular are polyoxyethylated ether and oleyl alcohol or its phosphonic ester, polyethoxylated lauryl alcohol, polyethoxylated oleyl alcohol, oxyethylated cetyl alcohol and various polyoxythylene glycols of fatty acids.

The compositions in gel form can also contain a coupling agent such as 2-ethylhexane-1,3-diol, a polyhydric alcohol such as sorbitol, a polyethylene glycol, lanolin or lanolin alcohol, as well as preserving agents.

According to a fourth embodiment of the compositions according to the invention, they are in the form of a lotion.

The vehicle for these lotions is either an aqueous solution or an aqueous-alcoholic solution containing, in substantially equal parts, deionized water and an alcohol such as ethanol or isopropanol.

The lotions can also contain at least one substance chosen from an isopropyl ester and a polyalkylene glycol or the oleate thereof.

According to a final embodiment of the compositions according to the invention, they are in the form of a lacquer and more particularly of an aerosol hair lacquer.

The cosmetically acceptable vehicle generally used in the lacquers consists of an alcohol such as ethanol or isopropanol or an aqueous-alcoholic mixture.

The lacquers according to this specific embodiment also contain at least one film-forming resin, at least one plasticizer and a propellant.

The film-forming resins used in the lacquers are well known in the prior art and mention may be made in particular of those described in patent FR-2 684 874, and they are preferably present in a proportion of from 3% to 6% by weight relative to the total weight of the composition.

Among the preferred plasticizers which may be mentioned in particular are glycol ethers, benzyl alcohol, triethyl citrate, 1,3-butylene glycol and propylene carbonate, which are present in a proportion of between X % and Y % by weight relative to the total weight of the composition.

The propellant for the lacquers can be chosen from at least one of the agents listed above for preparing compositions in the form of a mousse.

The lacquers according to this embodiment can also contain other conventional ingredients, such as corrosion inhibitors, softeners, fragrances, silicones, sunscreens, dyes, preserving agents, anti-foaming agents and vitamins.

After introducing the composition or "fluid" into a suitable container, the container is fitted with a suitable valve and diffusion system.

Among the valves which can be used, mention may be made in particular of those described in patent FR-2 382 637.

A subject of the present invention is also a repairing care and treatment process for keratin fibres, referred to hereinabove as a "direct" treatment process, this process consisting in applying to the keratin fibres a composition as defined above containing at least one polyamino acid derivative, and in leaving the composition to act on the fibres, optionally followed by rinsing the keratin fibres.

According to one particularly preferred embodiment of the repairing care and treatment process of the keratin fibres, referred to hereinabove as the "in-situ" treatment process, the polyamino acid derivative of formula (I) is formed "in situ", i.e. directly on the keratin fibres which are subjected to the treatment, with the aid of precursors which generate the polyamino acid derivative.

These precursors are, on the one hand, an N-carboxyanhydride of formula (II) and, on the other hand, a nucleophilic compound of formula (III) which, to carry out the treatment, are in the form of a packaging in two parts.

The first part contains at least one N-carboxyanhydride of formula (II) in solid form or diluted in a cosmetically acceptable vehicle, and the second part contains a nucleophilic compound of formula (III), in solid form or diluted in a cosmetically acceptable vehicle.

The cosmetically acceptable vehicle for the N-carboxyanhydride of formula (II) is an organic solvent, water or a mixture thereof. The cosmetically acceptable vehicle for the nucleophilic compound of formula (III) is preferably water.

The "in-situ" treatment process consists, in a first stage, in applying to the hair, which has optionally been moistened beforehand, the first part of the packaging, after optional dilution using a liquid medium, and then, in a second stage, in applying the second part of the packaging, also after optional dilution, in particular water-based dilution.

According to this process, if so desired, the two parts can be premixed and the solution obtained can be applied directly to the hair.

The hair is then rubbed, which brings about, in aqueous medium, the polycondensation of the precursors as a polyamino acid derivative. The polycondensation is generally complete after a period of about 2 to 30 minutes.

After this period of time, the hair is rinsed and optionally shampooed.

Examples of the preparation of the polyamino acid derivatives and examples of cosmetic compositions and of a hair treatment process will now be given by way of illustration.

EXAMPLES

Example 1

Preparation of the polyamino acid of formula (I) in which

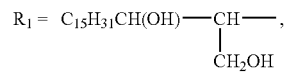

$X=\text{—NH—}$, $R_2=H$, $R_3=\text{—CH}_3$ and $n=14.2$.

46 g (0.4 mol) of sarcosine N-carboxyanhydride are suspended in 250 cm³ of toluene, under a nitrogen atmosphere, in a 1-litre reactor equipped with a condenser, a thermometer, a nitrogen inlet, an addition funnel and a stirrer. A suspension of 8.2 g (0.027 mol) of (D/L, erythro-threo) 2-aminooctadecane-1,3-diol in 250 cm³ of toluene is then added portionwise. After the end of the addition, the reaction mixture is maintained at 80° C. for about 3 hours. It is then allowed to cool to room temperature and 200 cm³ of ethanol (98° C.) are added to dissolve the medium.

After evaporating off the solvents under reduced pressure and drying under vacuum, 34.5 g of a brown-coloured powder are obtained.

The "n" index was determined by NMR.

According to the same procedure as above, by varying the proportion of (DL)-2-aminooctadecane-1,3-diol, polyamino acid derivatives having the same structure but having the following "n" indices were obtained:

Example 1(a)

n=9.8

Example 1(b)

n=7.6

Example 2

Preparation of the polyamino acid of formula (I) in which

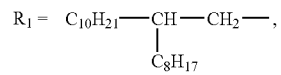

$X=\text{—NH—}$, $R_2=H$, $R_3=\text{—CH}_3$ and $n=14$.

46 g (0.4 mol) of sarcosine N-carboxyanhydride are suspended in 500 cm³ of toluene in a 1-litre reactor equipped with a condenser, a thermometer, a nitrogen inlet, an addition funnel and a stirrer. 8.1 g (0.027 mol) of 2-octyldodecylamine are then added dropwise. After the end of the addition, the mixture is maintained at 80° C. for about 2 hours. It is then allowed to cool to room temperature, followed by addition of 50 cm³ of ethanol (95° C.). After evaporating off the solvents under reduced pressure and drying under vacuum, 36.7 g of a brown-coloured powder are obtained.

The "n" index was determined by NMR.

According to the same procedure as above, but by varying the proportion of 2-octyldodecylamine, polyamino acid derivatives having the same structure but having the following "n" indices were obtained:

Example 2(a)

n=9.6

Example 2(b)

n=7.4

Example 3

Preparation of the polyamino acid of formula (I) in which $R_1=C_{16}H_{33}$, X=—NN—, $R_2$=H, $R_3$=—$CH_3$ and n=7.2.

This polyamino acid is obtained according to the same procedure as that described in Example 2, but by reacting 12 g (0.05 mol) of hexadecylamine with the sarcosine N-carboxyanhydride.

After evaporating off the solvents and drying under vacuum, 40 g of a powder are obtained.

By varying the proportion of hexadecylamine, polyamino acid derivatives having the same structure but having the following "n" indices were obtained:

Example 3(a)

n=9.2

Example 3(b)

n=12.5

Example 4

Preparation of a polyamino acid derivative of formula (I) in which $R_1=C_8H_{17}$—CH=CH—$C_8H_{16}$, X=—NH—, $R_2$=H, $R_3$=—$CH_3$ and n=7.4.

This polyamino acid is obtained according to the same procedure as that described in Example 2, but by reacting 13 g (0.05 mol) of oleylamine with the sarcosine N-carboxyanhydride.

After evaporating off the solvents and drying under vacuum, 42 g of a powder are obtained.

By varying the proportion of oleylamine, polyamino acid derivatives having the same structure but having the following "n" indices were obtained:

Example 4(a)

n=10.5

Example 4(b)

n=13.2

Example 5

Preparation of the polyamino acid of formula (I) in which

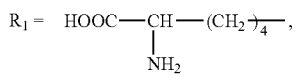

X=—NH—, $R_2$=H, $R_3$=—$CH_3$ and n=12.1.

10 g (0.08 mol) of sarcosine N-carboxyanhydride are placed in a 500 ml conical flask with stirring, followed by addition of 100 cm³ of distilled water (pH 6.7) and addition of 1 g (0.006 mol) of lysine in a single portion.

A considerable evolution of $CO_2$ is produced and stirring of the mixture is continued for about 30 minutes at room temperature. After evaporating off the water under reduced pressure and drying under vacuum, 6.7 g of a brown-coloured powder are obtained.

The "n" index was determined by NMR.

According to the same procedure as above, but varying the proportion of lysine, polyamino acid derivatives having the same structure but having the following theoretical "n" indices were obtained:

Example 5(a)

n=50

Example 5(b)

n=25

Example 5(c)

n=6

Example 5(d)

n=3

Example 6

Preparation of the polyamino acid of formula (I) in which

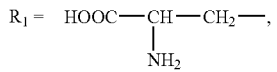

X=S, $R_2$=H, $R_3$=—$CH_3$ and n=13 (theoretical index).

This polyamino acid is obtained according to the same procedure as that described in Example 5, but replacing the lysine with the corresponding molar amount of cysteine.

Example 7

Preparation of the polyamino acid of formula (I) in which

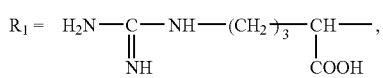

X=—NH—, $R_2$=H, $R_3$=—$CH_3$ and n=12 (theoretical index).

This polyamino acid is obtained according to the same procedure as that described in Example 5, but replacing the lysine with the corresponding molar amount of arginine.

Example 8

Preparation of the polyamino acid of formula (I) in which

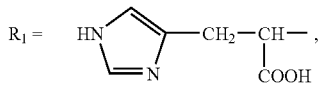

X=—NH—, $R_2$=H, $R_3$=—$CH_3$ and n=12 (theoretical index).

This polyamino acid is obtained according to the same procedure as that described in Example 5, but replacing the lysine with the corresponding molar amount of histidine.

Example 9

Preparation of the polyamino acid of formula (I) in which

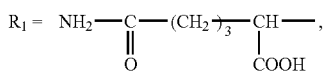

X=—NH—, $R_2$=H, $R_3$=—$CH_3$ and n=13 (theoretical index).

This polyamino acid is obtained according to the same procedure as that described in Example 5, but replacing the lysine with the corresponding molar amount of glutamine.

Example 10

Preparation of the polyamino acid of formula (I) in which

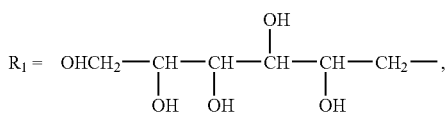

X=—NH—, $R_2$=H, $R_3$=—$CH_3$ and n=12 (theoretical index).

This polyamino acid is obtained according to the same procedure as that described in Example 5, but replacing the lysine with the corresponding molar amount of glucamine.

EXAMPLES OF COSMETIC COMPOSITIONS

The following formulations for hair care and hair treatment were prepared:

Example 11

Shampoo

| | |
|---|---|
| Sodium lauryl ether sulphate (28% A.M.) | 75 g |
| Coconut acid monoisopropanolamide sold by the company Albright & Wilson under the name "Empilan CIS ®" | 1 g |
| Polyamino acid of Example 5 | 1 g |
| Water q.s. | 100 g |

The shampoo thus formulated is of clear appearance.

Example 12

Rinse-out Hair Conditioner

| | |
|---|---|
| 1-methyl-2-tallow-3-sulphamidoethyl-imidazolium methosulphate/propene glycol (75/25) sold by the company Witco under the name "Rewoquat W75PG ®" | 2 g A.M. |
| Polyamino acid of Example 5 | 0.5 g |
| Oxyethylenated mixture of cetyl alcohol and cetylstearyl alcohol | 3 g |
| Preserving agent, fragrance, q.s. | |
| Spontaneous pH of 5.2 | |
| Water q.s. | 100 g |

Example 13

Shampoo

| | |
|---|---|
| Sodium lauryl ether sulphate (28% A.M.) | 60 g |
| Cocoyl betaine | 9 g |
| Polyamino acid of Example 1 | 0.5 g |
| Preserving agent, fragrance q.s. | |
| HCl q.s. pH 6 | |
| Water q.s. | 100 g |

The shampoo thus formulated is opalescent.

Example 14

Rinse-out Disentangling Lotion

| | |
|---|---|
| Behenyltrimethylammonium chloride at 80% in a water/isopropanol mixture (15/85) sold by the company Toho under the name "Catinal DC 50 ®" | 0.5 g A.M. |
| Polyamino acid of Example 4 | 0.1 g |
| Preserving agent, fragrance q.s. | |
| NaOH q.s. pH 5.5 | |
| Water q.s. | 100 g |

The examples which follow of strengthening treatment were carried out on the head ("in situ").

Example 15

Hair Treatment Process Using a Conditioner in Two Parts

A first conditioner containing a sarcosine N-carboxyanhydride solution diluted to 10% either in Soketal® (D,L-α, β-isopropylidene glycerol) or in dimethyl ether isosorbide, is first applied to hair which has been moistened beforehand. The solution thus applied should impregnate the hair entirely. Next, a second conditioner containing an L-lysine solution diluted to 4% in water is then applied. After leaving to act for 15 minutes, the hair is rinsed with warm water, shampooed and finally dried.

Example 16

Hair Treatment Process Using a Solid Conditioner in Two Parts

Sarcosine N-carboxyanhydride conditioned in solid form is first applied to hair which has been moistened beforehand and is then massaged for about 5 minutes. Next, an L-lysine solution diluted to 4% in water, packaged separately, is then added to the hair.

After leaving to act for about 15 minutes, the hair is rinsed with warm water, washed with a shampoo and dried.

The hair treated according to Example 15 or 16 shows a visible improvement in hold and volume.

COMPARATIVE TESTS

Study of the Keratin-fibre-strengthening Properties

The properties of strengthening natural hair and bleached hair were evaluated after treatment according to the "in-situ" process.

Locks of 0.6 g and of 15 cm of natural dark-chestnut hair, on the one hand, and of bleached hair, on the other hand, were first immersed in a phosphate buffer at 37° C., then rinsed with water and then shampooed and rinsed again.

One portion of the locks obtained serves as a control and the others were then treated using a solution prepared at the time of use by mixing 1 g of sarcosine N-carboxyanhydride (sarcosine NCA) and 0.1 g of lysine in a phosphate buffer at 37° C. After a period of about 30 minutes, in the course of which the polycondensation reaction takes place, the locks were then rinsed with water, after which they were shampooed and rinsed again.

The strengthening of the locks thus treated was quantified with the aid of the flexibility pendulum test. This flexibility pendulum test consists in measuring the number of oscillations of a pendulum having a ballast weight of 47 g which curves a sample of 39 hairs 10 mm in length. The hair-strengthening characteristics are inversely proportional to the number of oscillations of the pendulum. Specifically, any increase in the strengthening of the hair is reflected by a decrease in the number of oscillations of the pendulum.

The measurements of the number of oscillations on three samples of locks of natural and bleached hair, at a temperature of 25° C., and at a relative humidity of 45%, are given in Table 1 below:

TABLE 1

| Number of oscillations | Natural hair | Standard error | Bleached hair | Standard error |
|---|---|---|---|---|
| Control phosphate buffer | 159 | 2 | 130 | 2 |
| Sarcosine NCA/lysine (Test 1) | 148 | 2 | 125 | 1 |
| Sarcosine NCA/lysine (Test 2) | 149 | 2 | 130 | 1 |
| Sarcosine NCA/lysine (Test 3) | 150 | 1 | 125 | 1 |
| % variation | −6 | p = 0.0001 | −3 | p = 0.04 |

The difference observed in the number of oscillations between the natural hair and the bleached hair, before any treatment, can be explained essentially by the fact that bleaching gives rise to a large increase in the rigidity of the hair.

The results of Table 1 above show a reproducible decrease in the number of oscillations of the pendulum, of less than 6% for the natural hair, and of less than 3% for the bleached hair.

The "in-situ" treatment thus gives, after the polycondensation reaction, a significant increase in the intrinsic rigidity properties of natural and bleached hair. These characteristics are conserved and are always visible, even after the locks have been shampooed and then rinsed.

Quantification of the Deposition of Polylysine-sarcosine on Keratin Fibres

The deposition of polylysine-sarcosine was determined by assaying the amount of residual sarcosine on the surface of locks of natural or bleached hair after "direct" treatment and after "in-situ" treatment.

The quantification of the deposition of sarcosine was carried out after rinsing the treated locks, and after rinsing and shampooing the treated locks.

The locks of hair after these operations were subjected to an acid hydrolysis, and the amount of residual sarcosine was measured using a Hitachi L8500A amino acid autoanalyser.

The amounts of sarcosine found on the surface of the samples of natural and bleached hair are given in Table 2 below. These amounts are expressed in grams of sarcosine present on the hair per 100 grams of hair.

TABLE 2

| TREATMENTS | | | | | As g of sarcosine |
|---|---|---|---|---|---|
| | "In-situ" treatment | "Direct" treatment | After rinsing | After shampooing | per 100 g of hair |
| Control NATURAL HAIR | | + | | | 0 |
| | + | | + | + | 0.26 |
| | + | | + | | 0.32 |
| | | + | + | + | 0.16 |
| | | + | + | | 0.25 |
| Control BLEACHED HAIR | | + | | | 0 |
| | + | | + | + | 0.38 |
| | + | | + | | 0.67 |
| | | + | + | + | 0.36 |
| | | + | + | | 0.55 |

From Table 2 above, it may be observed that there is an appreciable sarcosine deposit after treatment and rinsing. This sarcosine deposit moreover remains in a satisfactory proportion after subsequent shampooing.

The invention claimed is:

1. A method for strengthening keratin fibers, comprising applying to said keratin fibers a cosmetic composition comprising at least one polyamino acid of formula (I):

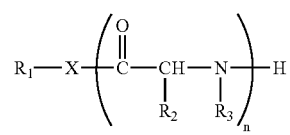

wherein
X is chosen from —O—, —S— and —NR$_5$—;
R$_1$ is

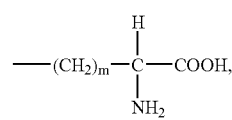

wherein m is 1 to 5;
R$_2$ is chosen from a hydrogen atom, C$_1$-C$_8$ alkyl groups, a —CH$_2$C$_6$H$_5$ group, a —CH$_2$C$_6$H$_5$ pOH group, wherein pOH is para-OH, a —CH$_2$OH group, a —CHOH—CH$_3$ group and —(CH$_2$)$_t$—NH$_2$ groups;
wherein t is chosen from 3, 4 and 5;

R₃ and R₅ which may be identical or different, are each chosen from a hydrogen atom and $C_1$-$C_6$ alkyl groups; and n is an average number greater than 1 such that the molecular weight of the polyamino acid of formula (I) ranges from 200 to 200,000, wherein the n repeating units may be identical or different;

or a salt of said polyamino acid.

2. The method according to claim 1, wherein said cosmetic composition comprises said at least one polyamino acid in an amount ranging from 0.001% to 30% by weight relative to the total weight of said cosmetic composition.

3. The method according to claim 1, wherein said cosmetic composition comprises said at least one polyamino acid in an amount ranging from 0.01% to 15% by weight relative to the total weight of the composition.

4. The method according to claim 1, wherein said cosmetic composition is in the form of a shampoo, said cosmetic composition further comprising a cosmetic vehicle chosen from aqueous solutions and aqueous-alcoholic solutions.

5. The method according to claim 4, wherein said shampoo further comprises at least one surfactant in an amount from 0.01% to 50% by weight relative to the total weight of the shampoo.

6. The method according to claim 1, wherein said cosmetic composition is in the form of a mousse, said cosmetic composition further comprising a cosmetic vehicle chosen from a fatty phase and aqueous-alcoholic solutions.

7. The method according to claim 6, wherein said mousse further comprises at least one foaming agent and at least one propellant.

8. The method according to claim 7, wherein said at least one DN foaming agent is present in an amount ranging from 0.05% to 20% by weight relative to the total weight of the mousse.

9. The method according to claim 7, wherein said at least one propellant is present in a proportion ranging from 1% to 20% by weight relative to the total weight of the mousse.

10. The method according to claim 1, wherein said cosmetic composition is in the form of a water-in-oil emulsion comprising a fatty phase present in an amount ranging from 30% to 50% by weight relative to the total weight of the composition.

11. The method according to claim 1, wherein said cosmetic composition is in the form of an oil-in-water emulsion comprising a fatty phase present in an amount ranging from 5% to 25% by weight relative to the total weight of the composition.

12. The method according to claim 10, wherein said cosmetic composition further comprises at least one emulsifier present in an amount ranging from 1% to 10% by weight relative to the total weight of the composition.

13. The method according to claim 11, wherein said cosmetic composition further comprises at least one emulsifier present in an amount ranging from 1% to 10% by weight relative to the total weight of the composition.

14. The method according to claim 11, wherein said oil-in-water emulsion is present in the form of a microemulsion or gel, the said fatty phase comprising at least one mineral oil.

15. The method according to claim 14, wherein said oil-in-water emulsion is present in the form of a gel and further wherein said at least one mineral oil is present in an amount ranging from 15% to 20% by weight relative to the total weight of the gel composition.

16. The method according to claim 1, wherein said cosmetic composition is in the form of a lotion comprising a cosmetic vehicle chosen from aqueous and aqueous-alcoholic solutions.

17. The method according to claim 1, wherein said cosmetic composition is in the form of a lacquer comprising a cosmetic vehicle chosen from alcohols and aqueous-alcoholic solutions.

18. The method according to claim 17, wherein said lacquer further comprises at least one film-forming resin, at least one plasticizer and at least one propellant.

19. The method according to claim 18, wherein said at least one film-forming resin is present in an amount from 3% to 6% by weight relative to the total weight of the lacquer.

20. The method according to claim 1, wherein said cosmetic composition further contains at least one conventional ingredient chosen from softeners, fragrances, plant and animal extracts, ceramides, silicones, sunscreens, dyes, antimicrobial agents, vitamins, preserving agents, sequestering agents, and pH regulators.

21. A method for strengthening keratin fibers comprising applying a composition to said fibers and optionally rinsing said keratin fibers, wherein said composition comprises:
at least one polyamino acid of formula (I):

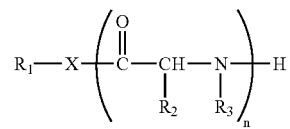

I wherein
X is chosen from —O—, —S— and —$NR_5$—;
$R_1$ is

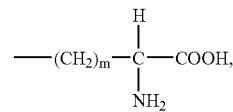

wherein m is 1 to 5;
$R_2$ is chosen from a hydrogen atom, $C_1$-$C_8$ alkyl groups, a —$CH_2C_6H_5$ group, a —$CH_2C_6H_5$ pOH group, wherein pOH is para-OH, a —$CH_2OH$ group, a —CHOH—$CH_3$ group and —$(CH_2)_t$—$NH_2$ groups, wherein t is chosen from 3, 4 and 5;
$R_3$ and $R_5$ which may be identical or different, are each chosen from a hydrogen atom and $C_1$-$C_6$ alkyl groups; and
n is an average number greater than 1 such that the molecular weight of the polyamino acid of formula (I) ranges from 200 to 200,000, wherein the n repeating units may be identical or different;
or a salt of said polyamino acid.

22. A method according to claim 21, comprising rinsing and subsequently shampooing said fibers.

23. A method according to claim 1, wherein said cosmetic composition further comprises a cosmetically acceptable vehicle.

24. The method according to claim 1, wherein said keratin fibers are hair.

25. A method according to claim 1, wherein said cosmetic composition further comprises at least one surfactant in an amount ranging from 0.05% to 30% by weight relative to the total weight of the composition.

26. A method according to claim 1, wherein said cosmetic composition further comprises a conditioner.

27. A method according to claim 20, wherein said at least one ingredient is present in an amount from 0.01% to 20% by weight relative to the total weight of the composition.

28. A method according to claim 27, wherein said at least one ingredient is present in an amount from 0.02% to 10% by weight relative to the total weight of the composition.

29. A method according to claim 1, further comprising rinsing following said applying.

30. A method according to claim 1, wherein n is an average number from 3 to 50, X is —NH—, $R_2$ is H, $R_3$ is —$CH_3$, and $R_1$ is

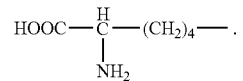

* * * * *

UNITED STATES PATENT AND TRADEMARK OFFICE
CERTIFICATE OF CORRECTION

PATENT NO. : 7,316,815 B2 Page 1 of 1
APPLICATION NO. : 10/682783
DATED : January 8, 2008
INVENTOR(S) : Michel Philippe et al.

It is certified that error appears in the above-identified patent and that said Letters Patent is hereby corrected as shown below:

Col. 15, line 34, delete "DN" after "one".

Signed and Sealed this

Twenty-fifth Day of March, 2008

JON W. DUDAS
*Director of the United States Patent and Trademark Office*